US00PP28708P3

(12) United States Plant Patent
Klemm et al.

(10) Patent No.: US PP28,708 P3
(45) Date of Patent: Nov. 28, 2017

(54) ***PELARGONIUM* PLANT NAMED 'KLEIZ15375'**

(50) Latin Name: ***Pelargonium* sp.**
Varietal Denomination: KLEIZ15375

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 79 days.

(21) Appl. No.: 14/998,908

(22) Filed: Mar. 2, 2016

(65) Prior Publication Data

US 2016/0360677 P1 Dec. 8, 2016

(30) Foreign Application Priority Data

Jun. 3, 2015 (CH) ..... PBR 15-3009

(51) Int. Cl.
*A01H 5/02* (2006.01)

(52) U.S. Cl.
USPC ..... Plt./324

(58) Field of Classification Search
USPC ..... Plt./324, 325, 330
See application file for complete search history.

(56) References Cited

PUBLICATIONS

UPOV hit on *Pelargonium* plant named 'Kleiz 15375', CH PBR 15-3009, application date Jun. 3, 2015.*
UPOV hit on *Pelargonium* plant named 'KLEIZ15375' QZ PBR 44839, application publication date Oct. 15, 2015.*

* cited by examiner

*Primary Examiner* — Anne M Grunberg
(74) *Attorney, Agent, or Firm* — Barbara Campbell; James M. Weatherly; Cochran Freund & Young, LLC

(57) ABSTRACT

A new *pelargonium* plant particularly distinguished by red flowers, an upright and compact growth habit, and strong branching, is disclosed.

1 Drawing Sheet

Genus and species: *Pelargonium* sp.
Variety denomination: 'KLEIZ15375'.

CROSS-REFERENCE TO RELATED APPLICATIONS

This application claims priority to and the benefit of Switzerland Plant Breeders Rights application filed on Jun. 3, 2015, Application No. 15-3009, the entire contents of which are incorporated herein by reference for all purposes.

An application with the European Community Plant Variety Office was filed on Jul. 1, 2015, File No. 2015-1521.

BACKGROUND OF THE NEW PLANT

The present invention comprises a new and distinct variety of *pelargonium*, botanically known as *Pelargonium* sp. and hereinafter referred to by the variety name 'KLEIZ15375'. 'KLEIZ15375' originated from a cross-combination in September 2010 in Stuttgart, Germany between the female *pelargonium* variety 'PIZ-2009-0725' (unpatented) and the proprietary male *pelargonium* variety 'PZ-2008-0129' (unpatented).

Seeds from the cross-combination in September 2010 in Stuttgart, Germany were obtained. The seeds were sown and plants were grown for evaluation. A single plant was selected in June 2011 and subsequently named 'KLEIZ15375'. In August 2011 'KLEIZ15375' was first vegetatively propagated by vegetative cuttings from stems. 'KLEIZ15375' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Red flowers;
2. An upright and compact growth habit; and
3. Strong branching.

DESCRIPTION OF THE PHOTOGRAPH

This new *pelargonium* plant is illustrated by the accompanying photograph which shows an overall view of the plant. The photograph is of an approximately ten-week-old plant grown in Stuttgart, Germany under greenhouse conditions in April 2014. The colors shown are as true as can be reasonably obtained by conventional photographic procedures.

DESCRIPTION OF THE NEW VARIETY

The following detailed descriptions set forth the distinctive characteristics of 'KLEIZ15375'. The data which define these characteristics were collected from asexual reproductions carried out in Stuttgart, Germany. Data was collected on plants grown 2-months after planting in Stuttgart, Germany under greenhouse conditions in May 2015. Color references are to The R.H.S. Colour Chart of The Royal Horticultural Society of London (R.H.S.), 5th edition (2007).

Classification:

*Family*.—Geraniaceae.

*Botanical*.—*Pelargonium* sp.

*Common*.—*Pelargonium*.

*Designation*.—'KLEIZ15375'.

Parentage:

*Female parent*.—The female *pelargonium* variety 'PIZ-2009-0725' (unpatented).

*Male parent*.—The proprietary male *pelargonium* variety 'PZ-2008-0129' (unpatented).

Plant:

*Form*.—Bushy and round.

*Habit*.—Upright and compact.

*Height*.—23.0 cm.

*Spread*.—25.0 cm.

*Natural flowering season*.—Spring to autumn.

*Propagation type*.—Vegetative cuttings.

*Time to produce a finished flowering plant*.—8 to 9 weeks.

*Time to initiate and develop roots*.—18 days.

*Root description*.—White, RHS 155D, and fine.

Stems:

*Quantity of stems per plant*.—5 to 6.

*Color*.—RHS 137A.

*Surface texture*.—Sparsely pubescent.

*Stem form*.—Round.

*Diameter*.—0.8 cm.

*Length*.—8.0 cm to 10.0 cm.

*Internode length*.—1.0 cm to 3.0 cm.

*Anthocyanin*.—Absent.

Leaves:

*Arrangement*.—Alternate.

*Shape*.—Kidney-shaped.

*Apex*.—Obtuse, round.

*Base*.—Open.

*Margin*.—Crenate.

*Surface texture*.—Upper surface: Rough, pubescent. Lower surface: Smooth, pubescent with very short hairs.

*Length*.—4.0 cm to 5.0 cm.

*Width*.—7.0 cm.

*Color*.—Upper surface: RHS 137A. Lower surface: RHS 137C.

*Petiole*.—Length: 5.0 cm to 6.0 cm. Diameter: 0.1 cm. Color: RHS 137B. Strength: Medium.

*Venation pattern*.—Palmate.

*Venation color*.—Upper surface: RHS 137B. Lower surface: RHS 137D.

*Zonation*.—Absent.

Inflorescence:

*Lastingness of flowers on the plant*.—5 to 6 days.

*Umbels*.—Quantity of umbels per plant: 6. Length: 5.0 cm. Diameter: 7.0 cm.

*Individual florets of the umbel*.—Quantity of florets per umbel: 6 to 8. Depth: 2.0 cm. Diameter: 3.5 cm.

*Fragrance*.—Absent.

Flower buds:

*Cluster shape*.—Round, ball-shaped.

*Cluster size*.—Length: 3.0 cm. Width: 3.0 cm.

*Surface texture*.—Rough, sparsely pubescent.

*Bud*.—Height: 1.0 cm to 1.5 cm. Width: 0.5 cm to 0.8 cm. Shape: Elliptic. Apex: Peaked. Base: Blunt. Margin: Entire. Color: RHS 137A.

Petals:

*Quantity per flower*.—6 and petaloids.

*Shape*.—Drop-shaped.

*Apex*.—Peaked.

*Base*.—Attenuate.

*Margin*.—Entire.

*Length*.—2.0 cm.

*Width*.—1.5 cm.

*Surface texture*.—Upper surface: Moderately pubescent. Lower surface: Moderately pubescent.

*Color of lobes*.—Upper lobes: Upper surface: RHS 44A. Lower surface: RHS 44C. Lower lobes: Upper surface: RHS 44A. Lower surface: RHS 44C.

Petaloids:

*Quantity per flower*.—1 to 3.

*Shape*.—Moderate.

*Apex*.—Round.

*Base*.—Attenuate.

*Margin*.—Entire.

*Texture* (*upper and lower surfaces*).—Smooth.

*Color*.—Upper surface: RHS 44A. Lower surface: RHS 44C.

Sepals:

*Number per flower*.—5.

*Shape*.—Elliptic.

*Apex*.—Peaked.

*Base*.—Obtuse.

*Margin*.—Entire.

*Surface texture*.—Upper surface: Moderately pubescent. Lower surface: Smooth.

*Color*.—Upper surface: RHS 137B and RHS 176C. Lower surface: RHS 137C.

*Length*.—0.8 cm.

*Width*.—0.3 cm.

Pedicel:

*Length*.—1.0 cm to 1.5 cm.

*Diameter*.—0.1 cm.

*Color*.—RHS 137B and RHS 176B.

*Surface texture*.—Moderately pubescent.

*Strength*.—Medium.

Peduncle:

*Length*.—9.0 cm to 12.0 cm.

*Diameter*.—0.4 cm.

*Color*.—RHS 137A.

*Surface texture*.—Rough, pubescent.

*Strength*.—Medium.

Reproductive organs:

*Stamens*.—Quantity of stamens per flower: 1 to a maximum of 5. Anther length: 0.15 cm. Filament length: 0.8 cm to 1.0 cm. Filament color: RHS 49D. Pollen amount: Moderate. Pollen color: RHS 25A.

*Pistils*.—Number: 1. Stigma color: RHS 66C. Style length: 0.6 cm. Style color: RHS 69D. Ovary arrangement: Central. Ovary color: RHS 138 C. Ovary diameter: 0.15 cm. Ovary length: 0.2 cm to 0.3 cm.

Fruit and seed set: None observed.

Disease and pest/insect resistance: None observed.

COMPARISON WITH PARENTAL LINES AND KNOWN VARIETY

'KLEIZ15375' is distinguished from its parents as described in Table 1:

TABLE 1

| Comparison with Parental Lines | | | |
|---|---|---|---|
| Characteristic | 'KLEIZ15375' | Female parent 'PIZ-2009-0725' | Male Parent 'PZ-2008-0129' |
| Flower color | Red | Orange | Dark-red |
| Growth | Compact | Compact | Strong |
| Branching | Strong | Strong | Medium |

'KLEIZ15375' can be compared to the commercial variety SUNRISE 'Fernando' (unpatented). Differences between the two varieties are described in Table 2:

TABLE 2

| Comparison with Similar Variety | | |
|---|---|---|
| Characteristic | 'KLEIZ15375' | Commercial line SUNRISE 'Fernando' |
| Branching | Strong | Medium |
| Earliness of flowering | Very-early | 14 days later than 'KLEIZ15375' |

We claim:

1. A new and distinct variety of *pelargonium* plant named 'KLEIZ15375' as illustrated and described herein.

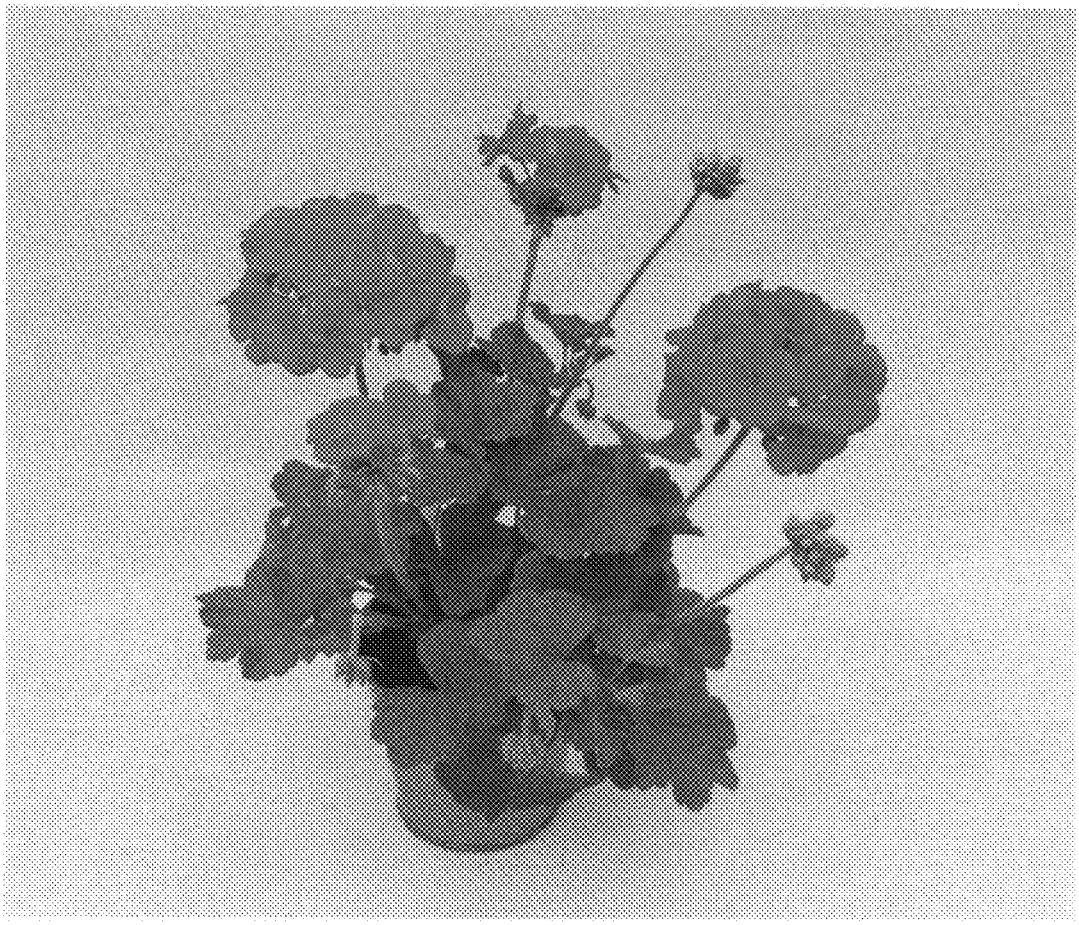

* * * * *